United States Patent
Bayer

(10) Patent No.: US 8,287,446 B2
(45) Date of Patent: Oct. 16, 2012

(54) VIBRATORY DEVICE, ENDOSCOPE HAVING SUCH A DEVICE, METHOD FOR CONFIGURING AN ENDOSCOPE, AND METHOD OF REDUCING LOOPING OF AN ENDOSCOPE

(75) Inventor: Lex Bayer, Palo Alto, CA (US)

(73) Assignee: Avantis Medical Systems, Inc., Sunnyvale, CA (US)

( * ) Notice: Subject to any disclaimer, the term of this patent is extended or adjusted under 35 U.S.C. 154(b) by 1313 days.

(21) Appl. No.: 11/736,438

(22) Filed: Apr. 17, 2007

(65) Prior Publication Data

US 2007/0244354 A1    Oct. 18, 2007

Related U.S. Application Data

(60) Provisional application No. 60/793,051, filed on Apr. 18, 2006.

(51) Int. Cl.
*A61B 1/00* (2006.01)
*A61B 1/04* (2006.01)

(52) U.S. Cl. .......................... 600/104; 600/114; 600/144

(58) Field of Classification Search .................. 600/141, 600/146
See application file for complete search history.

(56) References Cited

U.S. PATENT DOCUMENTS

| | | | |
|---|---|---|---|
| 3,437,747 A | 4/1969 | Sheldon | |
| 3,610,231 A | 10/1971 | Takahashi et al. | |
| 3,643,653 A | 2/1972 | Takahashi et al. | |
| 3,739,770 A | 6/1973 | Mori | |
| 3,889,662 A | 6/1975 | Mitsui | |
| 3,897,775 A | 8/1975 | Furihata | |
| 3,918,438 A | 11/1975 | Hayamizu et al. | |
| 4,261,344 A | 4/1981 | Moore et al. | |
| 4,351,587 A | 9/1982 | Matsuo et al. | |
| 4,398,811 A | 8/1983 | Nishioka et al. | |
| 4,494,549 A | 1/1985 | Namba et al. | |
| 4,573,450 A | 3/1986 | Arakawa | |
| 4,586,491 A | 5/1986 | Carpenter | |
| 4,625,236 A | 11/1986 | Fujimori et al. | |
| 4,646,722 A | 3/1987 | Silverstein et al. | |
| 4,699,463 A | 10/1987 | D'Amelio et al. | |
| 4,721,097 A | 1/1988 | D'Amelio | |
| 4,727,859 A | 3/1988 | Lia | |
| 4,741,326 A | 5/1988 | Sidall et al. | |
| 4,790,295 A | 12/1988 | Tashiro | |
| 4,800,870 A | 1/1989 | Reid, Jr. | |
| 4,825,850 A | 5/1989 | Opie et al. | |
| 4,836,211 A * | 6/1989 | Sekino et al. | 600/461 |

(Continued)

FOREIGN PATENT DOCUMENTS

CN    1 628 603    6/2005

(Continued)

OTHER PUBLICATIONS

International Search Report for PCT/US2008/069435, filed Jul. 8, 2008, mailed Oct. 23, 2008, 8 pgs.

(Continued)

*Primary Examiner* — Linda Dvorak
*Assistant Examiner* — Alireza Nia
(74) *Attorney, Agent, or Firm* — Morrison & Foerster LLP

(57) ABSTRACT

An endoscope assembly includes an insertion tube including a channel and a vibratory device inserted into the channel of the insertion tube.

11 Claims, 13 Drawing Sheets

U.S. PATENT DOCUMENTS

| | | | |
|---|---|---|---|
| 4,846,154 A | 7/1989 | MacAnally et al. | |
| 4,852,551 A | 8/1989 | Opie et al. | |
| 4,853,773 A | 8/1989 | Hibino et al. | |
| 4,862,873 A | 9/1989 | Yajima et al. | |
| 4,867,138 A | 9/1989 | Kubota et al. | |
| 4,869,238 A | 9/1989 | Opie et al. | |
| 4,870,488 A | 9/1989 | Ikuno et al. | |
| 4,873,572 A | 10/1989 | Miyazaki et al. | |
| 4,873,965 A | 10/1989 | Danieli | |
| 4,884,133 A | 11/1989 | Kanno et al. | |
| 4,899,732 A | 2/1990 | Cohen | |
| 4,905,667 A | 3/1990 | Foerster et al. | |
| 4,907,395 A | 3/1990 | Opie et al. | |
| 4,911,148 A | 3/1990 | Sosnowski et al. | |
| 4,911,564 A | 3/1990 | Baker | |
| 4,926,258 A | 5/1990 | Sasaki | |
| 4,947,827 A | 8/1990 | Opie et al. | |
| 4,947,828 A | 8/1990 | Carpenter et al. | |
| 4,979,496 A | 12/1990 | Komi | |
| 4,991,565 A | 2/1991 | Takahashi et al. | |
| 5,019,040 A | 5/1991 | Itaoka et al. | |
| 5,025,778 A | 6/1991 | Silverstein et al. | |
| 5,026,377 A | 6/1991 | Burton et al. | |
| 5,050,585 A | 9/1991 | Takahashi | |
| RE34,110 E | 10/1992 | Opie et al. | |
| 5,159,446 A * | 10/1992 | Hibino et al. | 348/65 |
| 5,166,787 A | 11/1992 | Irion | |
| 5,178,130 A | 1/1993 | Kaiya et al. | |
| 5,187,572 A | 2/1993 | Nakamura et al. | |
| 5,193,525 A | 3/1993 | Silverstein et al. | |
| 5,196,928 A | 3/1993 | Karasawa et al. | |
| 5,242,460 A * | 9/1993 | Klein et al. | 606/159 |
| 5,253,638 A | 10/1993 | Tamburrino et al. | |
| 5,260,780 A | 11/1993 | Staudt, III | |
| 5,271,381 A | 12/1993 | Ailinger et al. | |
| 5,305,121 A | 4/1994 | Moll | |
| 5,318,031 A | 6/1994 | Mountford et al. | |
| 5,329,887 A | 7/1994 | Ailinger et al. | |
| 5,337,734 A | 8/1994 | Saab | |
| 5,381,784 A | 1/1995 | Adair | |
| 5,398,685 A | 3/1995 | Wilk et al. | |
| 5,406,938 A | 4/1995 | Mersch et al. | |
| 5,434,669 A | 7/1995 | Tabata et al. | |
| 5,443,781 A | 8/1995 | Saab | |
| 5,447,148 A | 9/1995 | Oneda et al. | |
| 5,483,951 A | 1/1996 | Frassica et al. | |
| 5,494,483 A | 2/1996 | Adair | |
| 5,518,501 A | 5/1996 | Oneda et al. | |
| 5,520,607 A | 5/1996 | Frassica et al. | |
| 5,530,238 A | 6/1996 | Meulenbrugge et al. | |
| 5,533,496 A | 7/1996 | De Faria-Correa et al. | |
| 5,536,236 A | 7/1996 | Yabe et al. | |
| 5,556,367 A | 9/1996 | Yabe et al. | |
| 5,584,843 A * | 12/1996 | Wulfman et al. | 606/159 |
| 5,613,936 A | 3/1997 | Czarnek et al. | |
| 5,614,943 A | 3/1997 | Nakamura et al. | |
| 5,626,553 A | 5/1997 | Frassica et al. | |
| 5,634,466 A | 6/1997 | Gruner | |
| 5,653,677 A | 8/1997 | Okada et al. | |
| 5,667,476 A | 9/1997 | Frassica et al. | |
| 5,679,216 A | 10/1997 | Takayama et al. | |
| 5,681,260 A * | 10/1997 | Ueda et al. | 600/114 |
| 5,682,199 A | 10/1997 | Lankford | |
| 5,685,822 A | 11/1997 | Harhen | |
| 5,692,729 A | 12/1997 | Harhen | |
| 5,696,850 A | 12/1997 | Parulski et al. | |
| 5,702,348 A | 12/1997 | Harhen | |
| 5,706,128 A | 1/1998 | Greenberg | |
| 5,711,299 A | 1/1998 | Manwaring et al. | |
| 5,722,933 A | 3/1998 | Yabe et al. | |
| 5,752,912 A | 5/1998 | Takahashi et al. | |
| 5,762,603 A | 6/1998 | Thompson | |
| 5,817,061 A | 10/1998 | Goodwin et al. | |
| 5,827,177 A | 10/1998 | Oneda et al. | |
| 5,833,603 A | 11/1998 | Kovacs et al. | |
| 5,843,103 A * | 12/1998 | Wulfman | 606/159 |
| 5,860,914 A | 1/1999 | Chiba et al. | |
| 5,876,329 A | 3/1999 | Harhen | |
| 5,911,694 A * | 6/1999 | Ikeda et al. | 600/587 |
| 5,916,147 A | 6/1999 | Boury | |
| 5,924,977 A | 7/1999 | Yabe et al. | |
| 5,938,587 A | 8/1999 | Taylor et al. | |
| 5,982,932 A | 11/1999 | Prokoski | |
| 5,989,182 A | 11/1999 | Hori et al. | |
| 5,989,224 A | 11/1999 | Exline et al. | |
| 6,017,358 A | 1/2000 | Yoon | |
| 6,026,323 A | 2/2000 | Skladnev et al. | |
| 6,066,090 A | 5/2000 | Yoon | |
| 6,099,464 A | 8/2000 | Shimizu et al. | |
| 6,099,466 A | 8/2000 | Sano et al. | |
| 6,099,485 A | 8/2000 | Patterson | |
| 6,106,463 A | 8/2000 | Wilk | |
| 6,174,280 B1 | 1/2001 | Oneda et al. | |
| 6,190,330 B1 | 2/2001 | Harhen | |
| 6,214,028 B1 | 4/2001 | Yoon et al. | |
| 6,261,226 B1 | 7/2001 | McKenna et al. | |
| 6,261,307 B1 | 7/2001 | Yoon et al. | |
| 6,277,064 B1 | 8/2001 | Yoon | |
| 6,301,047 B1 | 10/2001 | Hoshino et al. | |
| 6,350,231 B1 | 2/2002 | Ailinger et al. | |
| 6,369,855 B1 | 4/2002 | Chauvel et al. | |
| 6,375,653 B1 | 4/2002 | Desai | |
| 6,387,043 B1 | 5/2002 | Yoon | |
| 6,433,492 B1 | 8/2002 | Buonavita | |
| 6,456,684 B1 | 9/2002 | Mun et al. | |
| 6,461,294 B1 | 10/2002 | Oneda et al. | |
| 6,482,149 B1 | 11/2002 | Torii | |
| 6,527,704 B1 | 3/2003 | Chang et al. | |
| 6,547,724 B1 | 4/2003 | Soble et al. | |
| 6,554,767 B2 | 4/2003 | Tanaka | |
| 6,564,088 B1 | 5/2003 | Soller et al. | |
| 6,640,017 B1 | 10/2003 | Tsai et al. | |
| 6,648,816 B2 | 11/2003 | Irion et al. | |
| 6,683,716 B1 | 1/2004 | Costales | |
| 6,687,010 B1 | 2/2004 | Horii et al. | |
| 6,697,536 B1 | 2/2004 | Yamada | |
| 6,699,180 B2 | 3/2004 | Kobayashi | |
| 6,736,773 B2 | 5/2004 | Wendlandt et al. | |
| 6,748,975 B2 | 6/2004 | Hartshorne et al. | |
| 6,796,939 B1 | 9/2004 | Hirata et al. | |
| 6,833,871 B1 | 12/2004 | Merrill et al. | |
| 6,845,190 B1 | 1/2005 | Smithwick et al. | |
| 6,891,977 B2 | 5/2005 | Gallagher | |
| 6,916,286 B2 | 7/2005 | Kazakevich | |
| 6,928,314 B1 | 8/2005 | Johnson et al. | |
| 6,929,636 B1 | 8/2005 | von Alten | |
| 6,947,784 B2 | 9/2005 | Zalis | |
| 6,951,536 B2 | 10/2005 | Yokoi et al. | |
| 6,965,702 B2 | 11/2005 | Gallagher | |
| 6,966,906 B2 | 11/2005 | Brown | |
| 6,974,411 B2 | 12/2005 | Belson | |
| 6,997,871 B2 | 2/2006 | Sonnenschein et al. | |
| 7,004,900 B2 | 2/2006 | Wendlandt et al. | |
| 7,029,435 B2 | 4/2006 | Nakao | |
| 7,041,050 B1 | 5/2006 | Ronald | |
| 7,095,548 B1 | 8/2006 | Cho et al. | |
| 7,103,228 B2 | 9/2006 | Kraft et al. | |
| 7,116,352 B2 | 10/2006 | Yaron | |
| 7,173,656 B1 | 2/2007 | Dunton et al. | |
| 7,228,004 B2 | 6/2007 | Gallagher et al. | |
| 7,280,141 B1 | 10/2007 | Frank et al. | |
| 7,322,934 B2 | 1/2008 | Miyake et al. | |
| 7,341,555 B2 | 3/2008 | Ootawara et al. | |
| 7,362,911 B1 | 4/2008 | Frank | |
| 7,405,877 B1 | 7/2008 | Schechterman | |
| 7,435,218 B2 | 10/2008 | Krattiger et al. | |
| 7,436,562 B2 | 10/2008 | Nagasawa et al. | |
| 7,507,200 B2 | 3/2009 | Okada | |
| 7,551,196 B2 | 6/2009 | Ono et al. | |
| 7,556,599 B2 | 7/2009 | Rovegno | |
| 7,561,190 B2 | 7/2009 | Deng et al. | |
| 7,621,869 B2 | 11/2009 | Ratnakar | |
| 7,646,520 B2 | 1/2010 | Funaki et al. | |
| 7,678,043 B2 | 3/2010 | Gilad | |
| 7,683,926 B2 | 3/2010 | Schechterman et al. | |
| 7,749,156 B2 | 7/2010 | Ouchi | |
| 7,825,964 B2 | 11/2010 | Hoshino et al. | |

| | | |
|---|---|---|
| 7,927,272 B2 | 4/2011 | Bayer et al. |
| 8,009,167 B2 | 8/2011 | Dekel et al. |
| 8,064,666 B2 | 11/2011 | Bayer |
| 8,070,743 B2 | 12/2011 | Kagan et al. |
| 2001/0007468 A1 | 7/2001 | Sugimoto et al. |
| 2001/0037052 A1 | 11/2001 | Higuchi et al. |
| 2001/0051766 A1 | 12/2001 | Gazdzinski |
| 2001/0056238 A1 | 12/2001 | Tsujita |
| 2002/0026188 A1 | 2/2002 | Balbierz et al. |
| 2002/0039400 A1 | 4/2002 | Kaufman et al. |
| 2002/0089584 A1 | 7/2002 | Abe |
| 2002/0095168 A1 | 7/2002 | Griego et al. |
| 2002/0099267 A1 | 7/2002 | Wendlandt et al. |
| 2002/0101546 A1 | 8/2002 | Sharp et al. |
| 2002/0110282 A1 | 8/2002 | Kraft et al. |
| 2002/0115908 A1 | 8/2002 | Farkas et al. |
| 2002/0156347 A1 | 10/2002 | Kim et al. |
| 2002/0193662 A1 | 12/2002 | Belson |
| 2003/0004399 A1 | 1/2003 | Belson |
| 2003/0011768 A1 | 1/2003 | Jung et al. |
| 2003/0032863 A1 | 2/2003 | Kazakevich |
| 2003/0040668 A1 | 2/2003 | Kaneko et al. |
| 2003/0045778 A1 | 3/2003 | Ohline et al. |
| 2003/0065250 A1 | 4/2003 | Chiel et al. |
| 2003/0088152 A1 | 5/2003 | Takada |
| 2003/0093031 A1 | 5/2003 | Long et al. |
| 2003/0093088 A1 | 5/2003 | Long et al. |
| 2003/0103199 A1 | 6/2003 | Jung et al. |
| 2003/0105386 A1 | 6/2003 | Voloshin et al. |
| 2003/0120130 A1 | 6/2003 | Glukhovsky |
| 2003/0125630 A1 | 7/2003 | Furnish |
| 2003/0125788 A1 | 7/2003 | Long |
| 2003/0130711 A1 | 7/2003 | Pearson et al. |
| 2003/0153866 A1 | 8/2003 | Long et al. |
| 2003/0161545 A1 | 8/2003 | Gallagher |
| 2003/0167007 A1 | 9/2003 | Belson |
| 2003/0171650 A1 | 9/2003 | Tartaglia et al. |
| 2003/0176767 A1 | 9/2003 | Long et al. |
| 2003/0179302 A1 | 9/2003 | Harada et al. |
| 2003/0187326 A1 | 10/2003 | Chang |
| 2003/0195545 A1 | 10/2003 | Hermann et al. |
| 2003/0197793 A1 | 10/2003 | Mitsunaga et al. |
| 2003/0225332 A1* | 12/2003 | Okada et al. .................. 600/439 |
| 2003/0225433 A1 | 12/2003 | Nakao |
| 2003/0233115 A1 | 12/2003 | Eversull et al. |
| 2004/0023397 A1 | 2/2004 | Vig et al. |
| 2004/0034278 A1 | 2/2004 | Adams |
| 2004/0049096 A1 | 3/2004 | Adams |
| 2004/0059191 A1 | 3/2004 | Krupa et al. |
| 2004/0080613 A1 | 4/2004 | Moriyama |
| 2004/0097790 A1 | 5/2004 | Farkas et al. |
| 2004/0109164 A1 | 6/2004 | Horii et al. |
| 2004/0111019 A1 | 6/2004 | Long |
| 2004/0122291 A1 | 6/2004 | Takahashi |
| 2004/0141054 A1 | 7/2004 | Mochida et al. |
| 2004/0158124 A1 | 8/2004 | Okada |
| 2004/0186350 A1* | 9/2004 | Brenneman et al. .......... 600/146 |
| 2004/0207618 A1 | 10/2004 | Williams et al. |
| 2004/0242987 A1 | 12/2004 | Liew et al. |
| 2005/0010084 A1 | 1/2005 | Tsai |
| 2005/0014996 A1 | 1/2005 | Konomura et al. |
| 2005/0020918 A1 | 1/2005 | Wilk et al. |
| 2005/0020926 A1 | 1/2005 | Wiklof et al. |
| 2005/0038317 A1 | 2/2005 | Ratnakar |
| 2005/0038319 A1 | 2/2005 | Goldwasser et al. |
| 2005/0068431 A1 | 3/2005 | Mori |
| 2005/0085693 A1 | 4/2005 | Belson et al. |
| 2005/0085790 A1 | 4/2005 | Guest et al. |
| 2005/0096502 A1 | 5/2005 | Khalili |
| 2005/0154278 A1 | 7/2005 | Cabiri et al. |
| 2005/0165272 A1 | 7/2005 | Okada et al. |
| 2005/0165279 A1 | 7/2005 | Adler et al. |
| 2005/0177024 A1 | 8/2005 | Mackin |
| 2005/0203420 A1 | 9/2005 | Kleen et al. |
| 2005/0215911 A1 | 9/2005 | Alfano et al. |
| 2005/0222500 A1 | 10/2005 | Itoi |
| 2005/0228224 A1 | 10/2005 | Okada et al. |
| 2005/0267361 A1 | 12/2005 | Younker et al. |
| 2005/0272975 A1 | 12/2005 | McWeeney et al. |
| 2005/0272977 A1 | 12/2005 | Saadat et al. |
| 2006/0044267 A1 | 3/2006 | Xie et al. |
| 2006/0052709 A1 | 3/2006 | DeBaryshe et al. |
| 2006/0058584 A1 | 3/2006 | Hirata |
| 2006/0106286 A1 | 5/2006 | Wendlandt et al. |
| 2006/0149127 A1 | 7/2006 | Seddiqui et al. |
| 2006/0149129 A1 | 7/2006 | Watts et al. |
| 2006/0149130 A1* | 7/2006 | Bob et al. .................. 600/114 |
| 2006/0183975 A1 | 8/2006 | Saadat et al. |
| 2006/0217594 A1 | 9/2006 | Ferguson |
| 2006/0279632 A1 | 12/2006 | Anderson |
| 2006/0285766 A1 | 12/2006 | Ali |
| 2006/0293562 A1 | 12/2006 | Uchimura et al. |
| 2007/0015967 A1 | 1/2007 | Boulais et al. |
| 2007/0015989 A1 | 1/2007 | Desai et al. |
| 2007/0083081 A1 | 4/2007 | Schlagenhauf et al. |
| 2007/0103460 A1 | 5/2007 | Zhang et al. |
| 2007/0135683 A1* | 6/2007 | Bob et al. .................. 600/144 |
| 2007/0142711 A1 | 6/2007 | Bayer et al. |
| 2007/0173686 A1 | 7/2007 | Lin et al. |
| 2007/0177008 A1 | 8/2007 | Bayer et al. |
| 2007/0177009 A1 | 8/2007 | Bayer et al. |
| 2007/0183685 A1 | 8/2007 | Wada et al. |
| 2007/0185384 A1 | 8/2007 | Bayer et al. |
| 2007/0225552 A1 | 9/2007 | Segawa et al. |
| 2007/0225734 A1 | 9/2007 | Bell et al. |
| 2007/0238927 A1 | 10/2007 | Ueno et al. |
| 2007/0270642 A1 | 11/2007 | Bayer et al. |
| 2007/0279486 A1 | 12/2007 | Bayer et al. |
| 2007/0280669 A1 | 12/2007 | Karim |
| 2007/0293720 A1 | 12/2007 | Bayer |
| 2008/0021269 A1 | 1/2008 | Tinkham et al. |
| 2008/0021274 A1 | 1/2008 | Bayer et al. |
| 2008/0033450 A1 | 2/2008 | Bayer et al. |
| 2008/0039693 A1 | 2/2008 | Karasawa |
| 2008/0064931 A1 | 3/2008 | Schena et al. |
| 2008/0065110 A1 | 3/2008 | Duval et al. |
| 2008/0071291 A1 | 3/2008 | Duval et al. |
| 2008/0079827 A1 | 4/2008 | Hoshino et al. |
| 2008/0097292 A1 | 4/2008 | Cabiri et al. |
| 2008/0114288 A1 | 5/2008 | Whayne et al. |
| 2008/0130108 A1 | 6/2008 | Bayer et al. |
| 2008/0154288 A1 | 6/2008 | Belson |
| 2008/0199829 A1 | 8/2008 | Paley et al. |
| 2008/0275298 A1 | 11/2008 | Ratnakar |
| 2009/0015842 A1 | 1/2009 | Leitgeb et al. |
| 2009/0023998 A1 | 1/2009 | Ratnakar |
| 2009/0036739 A1 | 2/2009 | Hadani |
| 2009/0049627 A1 | 2/2009 | Kritzler |
| 2009/0082629 A1 | 3/2009 | Dotan et al. |
| 2009/0105538 A1 | 4/2009 | Van Dam et al. |
| 2009/0137867 A1 | 5/2009 | Goto |
| 2009/0213211 A1 | 8/2009 | Bayer et al. |
| 2009/0231419 A1 | 9/2009 | Bayer |
| 2010/0217076 A1 | 8/2010 | Ratnakar |
| 2011/0160535 A1 | 6/2011 | Bayer et al. |
| 2011/0213206 A1 | 9/2011 | Boutillette et al. |

FOREIGN PATENT DOCUMENTS

| | | |
|---|---|---|
| CN | 1628603 A | 6/2005 |
| DE | 196 26 433 | 1/1998 |
| DE | 20 2006 017 173 U1 | 3/2007 |
| EP | 0 586 162 | 3/1994 |
| EP | 1 570 778 A1 | 9/2005 |
| EP | 1 769 720 A1 | 4/2007 |
| FR | 711 949 | 9/1931 |
| JP | 49-130235 A | 12/1974 |
| JP | 56-9712 A | 1/1981 |
| JP | 62-094312 U1 | 6/1987 |
| JP | 63-309912 A | 12/1988 |
| JP | 3-159629 A | 7/1991 |
| JP | 5-341210 A | 12/1993 |
| JP | 6-130308 A | 5/1994 |
| JP | 7-352 | 1/1995 |
| JP | 7-354 A | 1/1995 |
| JP | 7-021001 U | 4/1995 |
| JP | 8-206061 A | 8/1996 |
| JP | 7-136108 A | 5/1998 |
| JP | 11-76150 A | 3/1999 |

| | | |
|---|---|---|
| WO | WO 93/15648 | 8/1993 |
| WO | WO-99/17542 A1 | 4/1999 |
| WO | WO-99/30506 A1 | 6/1999 |
| WO | WO 02/085194 | 10/2002 |
| WO | WO-02/094105 A2 | 11/2002 |
| WO | WO-02/094105 A3 | 11/2002 |
| WO | WO-2006/073676 A1 | 7/2006 |
| WO | WO-2006/073725 A1 | 7/2006 |
| WO | WO-2006/110275 A2 | 10/2006 |
| WO | WO-2006/110275 A3 | 10/2006 |
| WO | WO-2007/015241 A2 | 2/2007 |
| WO | WO-2007/015241 A3 | 2/2007 |
| WO | WO-2007/070644 A2 | 6/2007 |
| WO | WO-2007/070644 A3 | 6/2007 |
| WO | WO-2007/087421 A2 | 8/2007 |
| WO | WO-2007/087421 A3 | 8/2007 |
| WO | WO-2007/092533 A2 | 8/2007 |
| WO | WO-2007/092533 A3 | 8/2007 |
| WO | WO-2007/092636 A2 | 8/2007 |
| WO | WO-2007/092636 A3 | 8/2007 |
| WO | WO-2007/136859 A2 | 11/2007 |
| WO | WO-2007/136859 A3 | 11/2007 |
| WO | WO-2007/136879 A2 | 11/2007 |
| WO | WO-2007/136879 A3 | 11/2007 |
| WO | WO-2007/136879 B1 | 11/2007 |
| WO | WO-2009/014895 A1 | 1/2009 |
| WO | WO-2009/015396 A2 | 1/2009 |
| WO | WO-2009/015396 A3 | 1/2009 |
| WO | WO-2009/049322 A2 | 4/2009 |
| WO | WO-2009/049322 A3 | 4/2009 |
| WO | WO-2009/062179 A1 | 5/2009 |

OTHER PUBLICATIONS

Invitation to Pay Additional Fees for PCT/US2008/071390, filed Jul. 28, 2008, mailed Nov. 11, 2008, 5 pgs.
U.S. Appl. No. 11/153,007, filed Jun. 14, 2005, Seddiqui et al.
U.S. Appl. No. 11/160,646, filed Jul. 1, 2005, Desai et al.
U.S. Appl. No. 11/215,660, filed Aug. 29, 2005, Watts et al.
U.S. Appl. No. 11/609,838, filed Dec. 12, 2006, Bayer et al.
U.S. Appl. No. 11/626,189, filed Jan. 23, 2007, Bayer et al.
U.S. Appl. No. 11/673,470, filed Feb. 9, 2007, Bayer et al.
U.S. Appl. No. 11/672,020, filed Feb. 6, 2007, Bayer et al.
U.S. Appl. No. 11/751,596, filed May 21, 2007, Bayer.
U.S. Appl. No. 11/751,597, filed May 21, 2007, Bayer et al.
U.S. Appl. No. 11/751,605, filed May 21, 2007, Diel et al.
International Search Report for PCT/US2005/044624, filed Dec. 8, 2005, mailed May 19, 2006, 16 pgs.
International Search Report for PCT/US2006/047748, filed Dec. 13, 2006, mailed Jun. 20, 2007, 12 pgs.
Invitation to Pay Additional Fees for PCT/US2007/002096, filed Jan. 23, 2007, mailed Jul. 6, 2007, 4 pgs.
Invitation to Pay Additional Fees for PCT/US2007/003631, filed Feb. 9, 2007, mailed Aug. 7, 2007, 5 pgs.
Invitation to Pay Additional Fees for PCT/US2007/003322, filed Feb. 6, 2007, mailed Aug. 7, 2007, 6 pgs.
U.S. Appl. No. 11/828,835, Bayer, filed Jun. 14, 2005.
U.S. Appl. No. 11/834,540, Bayer, filed Aug. 6, 2007.
Advisory Action mailed on Nov. 2, 2010, for U.S. Appl. No. 11/609,838, filed Dec. 12, 2006, 3 pages.
Advisory Action mailed on May 23, 2011, for U.S. Appl. No. 11/751,605, filed Action filed on May 21, 2007, 3 pages.
Amendment in Response to Non-Final Office Action filed on Jun. 29, 2009, U.S. Appl. No. 11/215,660, filed Aug. 29, 2005, 9 pages.
Amendment in Response to Final Office Action filed on Mar. 8, 2010, for U.S. Appl. No. 11/215,660, filed Aug. 29, 2005, 11 pages.
Amendment in Response to Non-Final Office Action filed on Jun. 25, 2010, for U.S. Appl. No. 11/609,838, filed Dec. 12, 2006, 14 pages.
Amendment in Response to Non-Final Office Action filed on Aug. 30, 2010, for U.S. Appl. No. 11/215,660, filed Aug. 29, 2005, 17 pages.
Amendment in Response to Final Office Action filed on Oct. 22, 2010, for U.S. Appl. No. 11/609,838, filed Dec. 12, 2006, 15 pages.
Amendment in Response to Non-Final Office Action filed on Oct. 22, 2010, for U.S. Appl. No. 11/834,540, filed Aug. 6, 2007, 13 pages.
Amendment in Response to Non-Final Office Action filed on Feb. 9, 2011, for U.S. Appl. No. 11/828,835, filed Jul. 26, 2007, 10 pages.
Amendment in Response to Non-Final Office Action filed on Feb. 25, 2011, for U.S. Appl. No. 11/751,605, filed May 21, 2007, 15 pages.
Amendment in Response to Final Office Action filed on Feb. 28, 2011, for U.S. Appl. No. 11/215,660, filed Aug. 29, 2005, 11 pages.
Amendment in Response to Non-Final Office Action filed on Apr. 12, 2011, for U.S. Appl. No. 11/626,189, filed Jan. 23, 2007, filed Jan. 23, 2007, 18 pages.
Amendment in Response to Non-Final Office Action filed on May 17, 2011, for U.S. Appl. No. 11/609,838, filed Dec. 12, 2006, 18 pages.
Amendment in Response to Final Office Action filed on May 17, 2011, for U.S. Appl. No. 11/751,605, filed May 21, 2007, 10 pages.
Amendment in Response to Final Office Action filed on May 24, 2011, for U.S. Appl. No. 11/828,835, filed Jul. 26, 2007, 13 pages.
Amendment in Response to Non-Final Office Action filed on Jun. 6, 2011, for U.S. Appl. No. 12/101,050, filed Apr. 10, 2008, 17 pages.
Amendment in Response to Final Office Action filed on Jun. 7, 2011, for U.S. Appl. No. 11/751,605, filed May 21, 2007, filed May 21, 2007, 11 pages.
European Communication mailed on Jan. 22, 2009, for European Application No. 07777255.6, filed on May 21, 2007, 2 pages.
European Office Action mailed on May 5, 2009, for European Patent Application No. 07763368.3, filed on Feb. 6, 2007, 3 pages.
European Office Action mailed on Feb. 5, 2010, for European Patent Application No. 06845440.4, filed on Dec. 13, 2006, 4 pages.
European Office Action mailed on Apr. 1, 2010, for European Patent Application No. 07717235.1, filed on Feb. 9, 2007, 2 pages.
European Office Action mailed on Nov. 8, 2010, for European Patent Application No. 05854262.2, filed on Dec. 8, 2005, 5 pages.
European Office Action mailed on Jun. 14, 2011, for European Patent Application No. 07795177.0, filed on May 21, 2007, 6 pages.
Final Office Action mailed on Aug. 23, 2010, for U.S. Appl. No. 11/609,838, filed Dec. 12, 2006, 20 pages.
Final Office Action mailed on Oct. 8, 2009, for U.S. Appl. No. 11/215,660, filed Aug. 29, 2005, 12 pages.
Final Office Action mailed on Mar. 22, 2011, for U.S. Appl. No. 11/828,835, filed 2007, 11 pages.
Final Office Action mailed on Apr. 29, 2011, for U.S. Appl. No. 11/751,605, filed May 21, 2007, 9 pages.
Final Office Action mailed on Nov. 1, 2010, for U.S. Appl. No. 11/215,660, filed Aug. 29, 2005, 12 pages.
International Search Report mailed on May 18, 2006, for PCT Patent Application No. PCT/US2005/045499, filed on Dec. 8, 2005, 4 pages.
International Search Report mailed on Sep. 28, 2007, for PCT Patent Application No. PCT/US2007/002096 filed on Jan. 23, 2007, 4 pages.
International Search Report mailed on Oct. 25, 2007, for PCT Patent Application No. PCT/US2007/003322, filed on Feb. 6, 2007, 5 pages.
International Search Report mailed on Oct. 26, 2007, for PCT Patent Application No. PCT/US2007/003631, filed on Feb. 9, 2007, 5 pages.
International Search Report mailed on Dec. 11, 2007, for PCT Patent Application No. PCT/US2007/012358, filed on May 21, 2007, 3 pages.
International Search Report mailed on Jan. 28, 2008, for PCT Patent Application No. PCT/US2007/012189, filed on May 21, 2007, 2 pages.
International Search Report mailed on Mar. 13, 2009, for PCT Patent Apllication No. PCT/US2008/083034, filed on Nov. 10, 2008, 3 pages.
International Search Report mailed on Feb. 25, 2009, for PCT Patent Application No. PCT/US2008/071390, filed on Jul. 28, 2008, 2 pages.
International Search Report mailed on Mar. 13, 2009, for PCT Patent Application No. PCT/US2008/079891, filed on Nov. 10, 2008, 2 pages.
International Search Report mailed on Apr. 6, 2009, for PCT Patent Application No. PCT/US2008/079878, filed on Oct. 14, 2008, 3 pages.
Invitation to Pay Additional Fees mailed on Dec. 29, 2008, for PCT Patent Application No. PCT/US2008/079891, filed on Oct. 14, 2008, 7 pages.

Japanese Office Action mailed on Jul. 19, 2011, for Japanese Patent Application No. 2007-550378, filed on Dec. 8, 2005, with English Translation, 11 pages.
Non-Final Office Action mailed on Jan. 10, 2008, for U.S. Appl. No. 11/160,646, filed Jul. 1, 2005, 6 pages.
Non-Final Office Action mailed on Mar. 12, 2008, for U.S. Appl. No. 11/153,007, filed Jun. 14, 2005, 11 pages.
Non-Final Office Action mailed on Mar. 25, 2009, for U.S. Appl. No. 11/215,660, filed Aug. 29, 2005, 11 pages.
Non-Final Office Action mailed on Mar. 29, 2010, for U.S. Appl. No. 11/215,660, filed Aug. 29, 2005, 16 pages.
Non-Final Office Action mailed on Apr. 6, 2010, U.S. Appl. No. 11/609,838, filed Dec. 12, 2006, 25 pages.
Non-Final Office Action mailed on Aug. 24, 2010, for U.S. Appl. No. 11/834,540, filed Aug. 6, 2007, 11 pages.
Non-Final Office Action mailed on Oct. 18, 2010, for U.S. Appl. No. 11/626,189, filed Jan. 23, 2007, 11 pages.
Non-Final Office Action mailed on Oct. 28, 2010, for U.S. Appl. No. 11/828,835, filed Jul. 26, 2007, 11 pages.
Non-Final Office Action mailed on Dec. 22, 2010, for U.S. Appl. No. 11/751,605, filed May 21, 2007, 10 pages.
Non-Final Office Action mailed on Feb. 17, 2011, for U.S. Appl. No. 11/609,838, filed Dec. 12, 2006, 24 pages.
Non-Final Office Action mailed on May 23, 2011, for U.S. Appl. No. 12/101,050, filed Apr. 10, 2008, 11 pages.
Non-Final Office Action mailed on Jun. 28, 2011, for U.S. Appl. No. 11/938,256, filed Nov. 10, 2007, 23 pages.
Non-Final Office Action mailed on Aug. 4, 2011, for U.S. Appl. No. 11/609,838, filed Dec. 12, 2006, 16 pages.
Non-Final Office Action mailed on Aug. 15, 2011, for U.S. Appl. No. 11/626,189, filed Jan. 23, 2007, 13 pages.
Non-Final Office Action mailed on Aug. 18, 2011, for U.S. Appl. No. 11/751,597, filed May 21, 2007, 25 pages.
Non-Final Office Action mailed on Sep. 9, 2011, U.S. Appl. No. 11/751,596, filed May 21, 2007, 6 pages.
Non-Final Office Action mailed on Oct. 21, 2011, for PCT Patent Application No. 12/251,406, filed Oct. 14, 2008, 8 pages.
Non-Final Office Action mailed on Oct. 26, 2011, for U.S. Appl. No. 11/673,470, filed Feb. 9, 2007, 40 pages.
Non-Final Office Action mailed on Nov. 23, 2011, for U.S. Appl. No. 11/672,020, filed Feb. 6, 2007, 12 pages.
Notice of Allowance mailed on Dec. 13, 2010, for U.S. Appl. No. 11/834,540, filed Aug. 6, 2007, 4 pages.
Notice of Allowance mailed on Jul. 22, 2011, for U.S. Appl. No. 12/101,050, filed Apr. 10, 2008, 7 pages.
Preliminary Amendment filed Jan. 26, 2009, for U.S. Appl. No. 11/672,020, filed Feb. 6, 2007, 11 pages.
Response to European Communication filed Feb. 6, 2009, for European Patent Application No. 07777255.6, filed on May 21, 2007, 5 pages.
Response to European Office Action filed on Nov. 11, 2009, for European Patent Application No. 07783368.3, filed on Feb. 6, 2007, 12 pages.
Response to European Office Action filed on Jul. 7, 2010, for European Patent Application No. 06845440.4, filed on Dec. 13, 2006, 13 pages.
Response to European Office Action filed on Aug. 18, 2010, for European Patent Application No. 07717235.1, filed on Feb. 9, 2007, 7 pages.
Response to European Office Action filed on Mar. 8, 2011, for European Patent Application No. 05854262.2, filed on Dec. 8, 2005, 11 pages.
Response to Restriction Requirement filed on Jan. 26, 2009, for U.S. Appl. No. 11/215,660, filed Aug. 29, 2005, 2 pages.
Response to Restriction Requirement filed on Jul. 23, 2010, for U.S. Appl. No. 11/751,605, filed May 21, 2007, 9 pages.
Response to Restriction Requirement filed on Aug. 4, 2010, for U.S. Appl. No. 11/834,540, filed Aug. 6, 2007, 5 pages.
Response to Restriction Requirement filed on Sep. 9, 2010, for U.S. Appl. No. 11/626,189, filed Jan. 23, 2007, 8 pages.
Response to Restriction Requirement filed on Oct. 21, 2010, for U.S. Appl. No. 11/828,835, filed Jul. 26, 2007, 7 pages.
Response to Restriction Requirement filed on Apr. 27, 2011, for U.S. Appl. No. 12/101,050, filed Apr. 10, 2008, 11 pages.
Response to Restriction Requirement filed on Jun. 16, 2011, for U.S. Appl. No. 11/751,596, filed May 21, 2007, 8 pages.
Response to Restriction Requirement filed on Oct. 31, 2011, for U.S. Appl. No. 11/672,020, filed Feb. 6, 2007, 3 pages.
Restriction Requirement mailed on Oct. 30, 2008, for U.S. Appl. No. 11/215,660, filed Aug. 29, 2005, 7 pages.
Restriction Requirement mailed on Jun. 25, 2010, for U.S. Appl. No. 11/751,605, filed May 21, 2007, 9 pages.
Restriction Requirement mailed on Jul. 13, 2010, for U.S. Appl. No. 11/834,540, filed Aug. 6, 2007, 8 pages.
Restriction Requirement mailed on Aug. 10, 2010, for U.S. Appl. No. 11/626,189, filed Jan. 23, 2007, 5 pages.
Restriction Requirement mailed on Sep. 21, 2010, for U.S. Appl. No. 11/828,835, filed Jul. 26, 2007, 6 pages.
Restriction Requirement mailed on Mar. 11, 2011, for U.S. Appl. No. 12/101,050, filed Apr. 10, 2008, 6 pages.
Restriction Requirement mailed on Jun. 6, 2011, for U.S. Appl. No. 11/751,596, filed May 21, 2007, 6 pages.
Restriction Requirement mailed on Sep. 29, 2011, for U.S. Appl. No. 11/672,020, filed on Feb. 6, 2007, 6 pages.
Restriction Requirement mailed on Nov. 28, 2011, for U.S. Appl. No. 12/251,383, filed on Oct. 14, 2008, 6 pages.
Substitute Preliminary Amendment filed Mar. 8, 2010, for U.S. Appl. No. 11/672,020, filed Feb. 6, 2007, 2 pages.
Written Opinion of the International Searching Authority mailed on May 18, 2006, for PCT Patent Application No. PCT/US2005/045499, filed on Dec. 8, 2005, 9 pages.
Written Opinion Patent Application of the International Searching Authority mailed on May 19, 2006, for PCT Patent Application No. PCT/US2005/044624, filed on Dec. 8, 2005, 8 pages.
Written Opinion of the International Searching Authority mailed on Jun. 20, 2007, for PCT Patent Application No. PCT/US2006/047748, filed on Dec. 13, 2006, 7 pages.
Written Opinion of the International Searching Authority mailed on Sep. 28, 2007, for PCT Patent Application No. PCT/US2007/002096, filed on Jan. 23, 2007, 8 pages.
Written Opinion of the International Searching Authority mailed on Oct. 25, 2007, for PCT Patent Application No. PCT/US2007/003322, filed on Feb. 6, 2007, 9 pages.
Written Opinion of the International Searching Authority mailed on Oct. 26, 2007, for PCT Patent Application No. PCT/US2007/003631, filed on Feb. 9, 2007, 7 pages.
Written Opinion of the International Searching Authority mailed on Dec. 11, 2007, for PCT Patent Application No. PCT/US2007/012358, filed on May 21, 2007, 6 pages.
Written Opinion of the International Searching Authority mailed on Jan. 28, 2008, for PCT Patent Application No. PCT/US2007/012189, filed on May 21, 2007, 7 pages.
Written Opinion of the International Searching Authority mailed on Oct. 23, 2008, for PCT Patent Application No. PCT/US2008/069435, filed on Jul. 8, 2008, 6 pages.
Written Opinion of the International Searching Authority mailed on Feb. 25, 2009, for PCT Patent Application No. PCT/US2008/071390, filed on Jul. 28, 2008, 7 pages.
Written Opinion of the International Searching Authority mailed on Mar. 13, 2009, for PCT Patent Application No. PCT/US2008/083034, filed on Nov. 10, 2008, 4 pages.
Written Opinion of International Searching Authority mailed on Mar. 13, 2009, for PCT Patent Application No. PCT/US2008/079891, filed on Nov. 10, 2008, 5 pages.
Written Opinion of International Searching Authority mailed on Apr. 6, 2009, for PCT Patent Application No. PCT/US2008/079878, filed on Oct. 14, 2008, 13 pages.
Amendment in Response to Non-Final Office Action filed on Dec. 16, 2011, for U.S. Appl. No. 11/938,256, filed Nov. 10, 2007, 10 pages.
Amendment in Response to Non-Final Office Action filed on Jan. 9, 2012, for U.S. Appl. No. 11/751,596, filed May 21, 2007, 9 pages.
Amendment in Response to Non-Final Office Action filed on Feb. 15, 2012, for U.S. Appl. No. 11/626,189, filed Jan. 23, 2007, 13 pages.

Amendment in Response to Non-Final Office Action filed on Feb. 17, 2012, for U.S. Appl. No. 11/751,597, filed May 21, 2007, 18 pages.
Non-Final Office Action mailed on Feb. 13, 2012, for U.S. Appl. No. 13/275,206, filed Oct. 17, 2011, 13 pages.
Non-Final Office Action mailed on Feb. 14, 2012, for U.S Appl. No. 12/251,383, filed Oct. 14, 2008, 9 pages.
Notice of Allowance mailed on Feb. 8, 2012, for U.S. Appl. No. 11/609,838, filed Dec. 12, 2006, 8 pages.
Response to European Office Action filed on Dec. 13, 2011, for European Patent Application No. 07795177.0, filed on May 21, 2007, 9 pages.

* cited by examiner

VIBRATORY DEVICE, ENDOSCOPE HAVING SUCH A DEVICE, METHOD FOR CONFIGURING AN ENDOSCOPE, AND METHOD OF REDUCING LOOPING OF AN ENDOSCOPE

This application claims the benefit of U.S. Provisional Patent Application No. 60/793,051, filed Apr. 18, 2006, the entire disclosure of which is incorporated herein by reference.

TECHNICAL FIELD OF THE INVENTION

The present invention relates to a vibratory device, an endoscope having such a vibratory device, a method for configuring an endoscope, and a method of reducing looping of an endoscope.

BACKGROUND OF THE INVENTION

There are many types of endoscopes, and they are named in relation to the organs or areas with which they are used. For example, gastroscopes are used for examination and treatment of the esophagus, stomach and duodenum; endoscope for the colon; bronchoscopes for the bronchi; laparoscopes for the peritoneal cavity; sigmoidoscopes for the rectum and the sigmoid colon; arthroscopes for joints; cystoscopes for the urinary bladder; and angioscopes for the examination of blood vessels.

A conventional endoscope is a medical device comprising a flexible tube, which is insertable into an internal body cavity through a body orifice to examine the body cavity and tissues for diagnosis. An endoscope may include a camera and a light source mounted on the distal end of its flexible tube. The tube of the endoscope has one or more longitudinal channels, through which an instrument can reach the body cavity to take samples of suspicious tissues or to perform other surgical procedures such as polypectomy.

To insert an endoscope into an internal body cavity, a physician advances the endoscope's flexible tube towards the body cavity with the distal end of the flexible tube at the front. The flexible tube may be steered to follow the cavity's contour by controlling a bendable distal end portion of the flexible tube. The advancement of the flexible tube in this manner may lead to a problem known as "looping." As the flexible tube is inserted farther and farther into the body cavity, it becomes more difficult to advance the flexible tube. At each turn, the flexible tube must maintain the same curve as the body cavity. In some instances, the flexible tube rubs against the inner surface of the body cavity along the outside of a turn. This rubbing creates a frictional force that causes the flexible tube to loop rather than advancing forward. The loop, subsequently, pushes against the body cavity, causing the patient pain and discomfort. In cases of extreme tortuosity, it may become impossible to advance the flexible tube to reach the desired location in the body cavity. In some situations, looping of the flexible tube can create perforations in the body cavity.

Therefore, there is a need to reduce or prevent the problem of "looping." A solution to the problem would allow for a more widespread use of the procedure and would improve its efficiency.

SUMMARY OF THE INVENTION

In a preferred embodiment of the present invention, a vibratory device may be used to vibrate the insertion tube of the endoscope to prevent the buildup of looping-causing frictional forces when the insertion tube is being advanced into a body cavity. Since the insertion tube is vibrating, any given segment of the insertion tube is only in contact with the body cavity for a brief moment of time. This prevents frictional forces from causing looping.

In accordance with one aspect of the invention, a vibratory device for an endoscope includes a motor, a flexible transmission cable having a longitudinal axis, and a plurality of masses. The flexible transmission cable is connected to the motor for the motor to rotate the flexible transmission cable about its longitudinal axis. Each mass preferably is attached to the flexible transmission cable in a manner that its center of mass is offset from the longitudinal axis of the flexible transmission cable. In a preferred embodiment, each mass includes two portions, one of the portions having a greater density or weight than the other portion.

The flexible transmission cable may include a first section connected to the motor and a second section connected to the first section, and the first section may have a larger cross-section than the second section. In some cases, the masses are attached only to the second section of the flexible transmission cable.

In accordance with another aspect of the invention, a vibratory device for an endoscope includes a flexible transmission cable having a layer of metal wire, a core disposed within the layer of metal wire, and a plurality of masses disposed between the layer of metal wire and the core. Preferably, each mass is attached to the flexible transmission cable in a manner that each mass's center of mass is offset from a longitudinal axis of the transmission cable.

In accordance with still another aspect of the invention, a vibratory device for an endoscope includes a flexible transmission cable having a longitudinal axis and a plurality of masses attached to the flexible transmission cable. Preferably, each mass includes two portions, and one of the portions has a greater density than the other portion so that each mass's center of mass is offset from the longitudinal axis of the cable. In some embodiments, the flexible transmission cable include a plurality of segments and a plurality of connectors, and each connector connects two segments and includes one of the masses. The vibratory device may also include a motor connected to the flexible transmission cable such that the motor rotates the flexible transmission cable about a longitudinal axis of the flexible transmission cable. Preferably, the flexible transmission cable includes a first section connected to the motor and a second section connected to the first section, and the masses are attached to the second section of the flexible transmission cable.

In accordance with yet another aspect of the invention, a vibratory device for an endoscope includes a flexible transmission cable having a longitudinal axis and a plurality of mass assemblies attached to the flexible transmission cable. Preferably, each mass assembly includes a housing and a mass disposed in the housing, and each mass assembly's center of mass is offset from the longitudinal axis of the cable.

In accordance with still yet another aspect of the invention, a vibratory device for an endoscope includes a flexible transmission cable including a plurality of segments and a plurality of connectors, and each connector connects two segments and includes a mass whose center of mass is offset from a longitudinal axis of the transmission cable.

In accordance with a further aspect of the invention, a vibratory device for an endoscope includes a flexible transmission cable including a first section and a second section connected to the first section, and a power switch positioned adjacent the connection between the first and second sections.

In accordance with a still further aspect of the invention, a vibratory device for an endoscope includes a flexible transmission cable including a first section and a second section connected to the first section, and a seal positioned adjacent the connection between the first and second sections.

In accordance with a yet further aspect of the invention, an endoscope assembly includes an insertion tube including a channel, and a vibratory device inserted into the channel of the insertion tube. In some embodiments, the insertion tube and the vibratory device are integrally formed. In a preferred embodiment, the vibratory device may be any of the vibratory devices described above.

In accordance with a still yet further aspect of the invention, a method for configuring an endoscope includes inserting a vibratory device into a channel of an endoscope. The method may include also the step of connecting a torque transmission cable of the vibratory device to a motor assembly of the vibratory device. The method may further include the step of powering on a motor of the motor assembly. Additionally, the inserting step may include inserting the vibratory device into only a non-steerable region of the endoscope.

In accordance with a still further aspect of the invention, a method for reducing looping of an endoscope includes inserting an endoscope into a body cavity and powering on a motor of a vibratory device of the endoscope to transmit vibration from the vibratory device to the endoscope to reduce looping of the endoscope. The method may further include inserting the vibratory device into a channel of the endoscope before inserting the endoscope into the body cavity. Alternatively, the method may further include inserting the vibratory device into a channel of the endoscope after inserting the endoscope into the body cavity and/or after looping has taken place.

DETAILED DESCRIPTION OF EMBODIMENTS OF THE INVENTION

Figure 1:
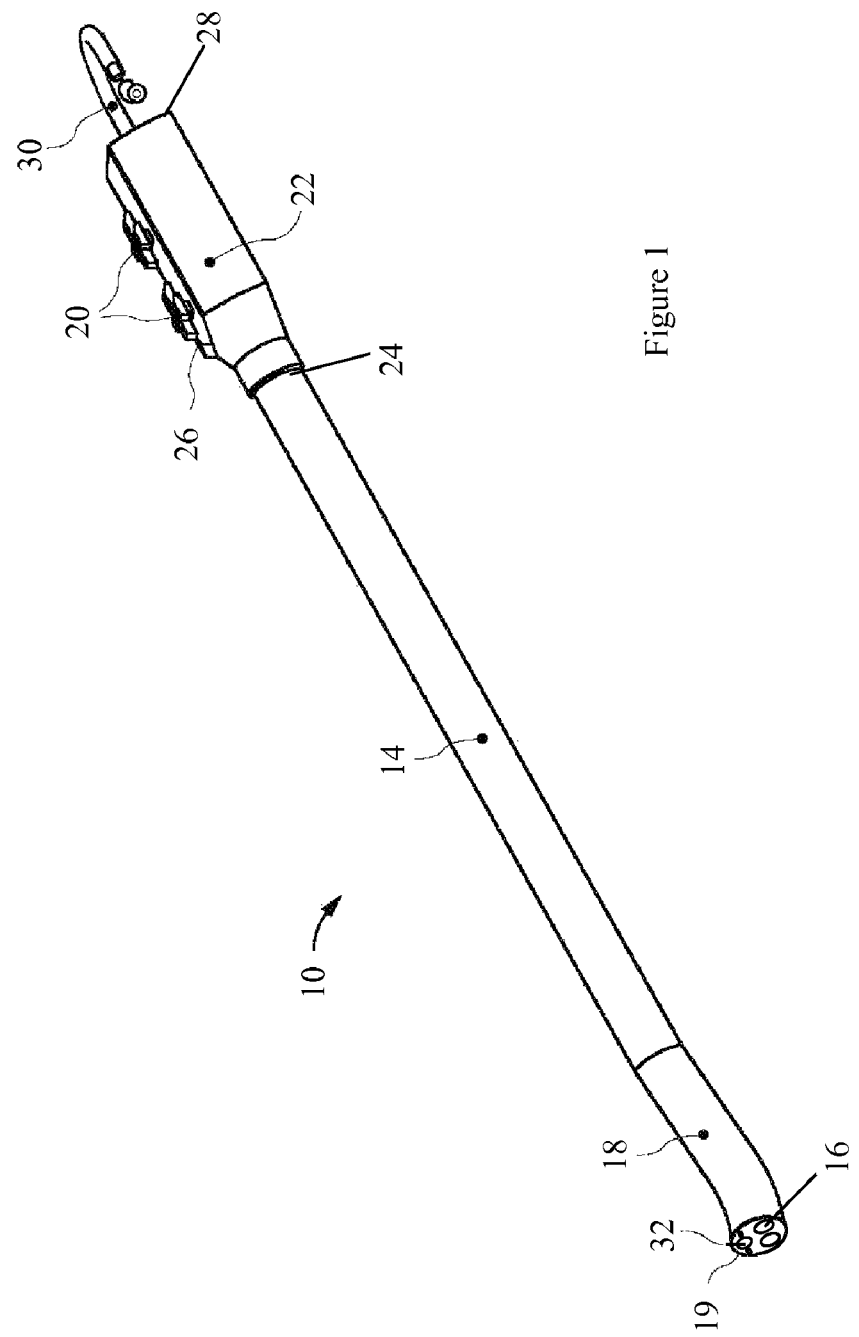
FIG. 1 shows a perspective view of an endoscope (without a vibratory device) according to one embodiment of the present invention.

FIG. 1 illustrates an exemplary endoscope 10 of the present invention. This endoscope 10 can be used in a variety of medical procedures in which imaging of a body tissue, organ, cavity or lumen is required. The types of procedures include, for example, anoscopy, arthroscopy, bronchoscopy, colonoscopy, cystoscopy, EGD, laparoscopy, and sigmoidoscopy.

The endoscope 10 includes a vibratory device 12 (FIG. 3) that is insertable into an insertion tube 14 of the endoscope 10. The vibratory device 12 is used to generate vibrations that are transmitted to the insertion tube 14. The vibrations reduce the possibility of looping of the insertion tube 14 by reducing the buildup of frictional forces between the body cavity and the insertion tube 14.

Figure 2:
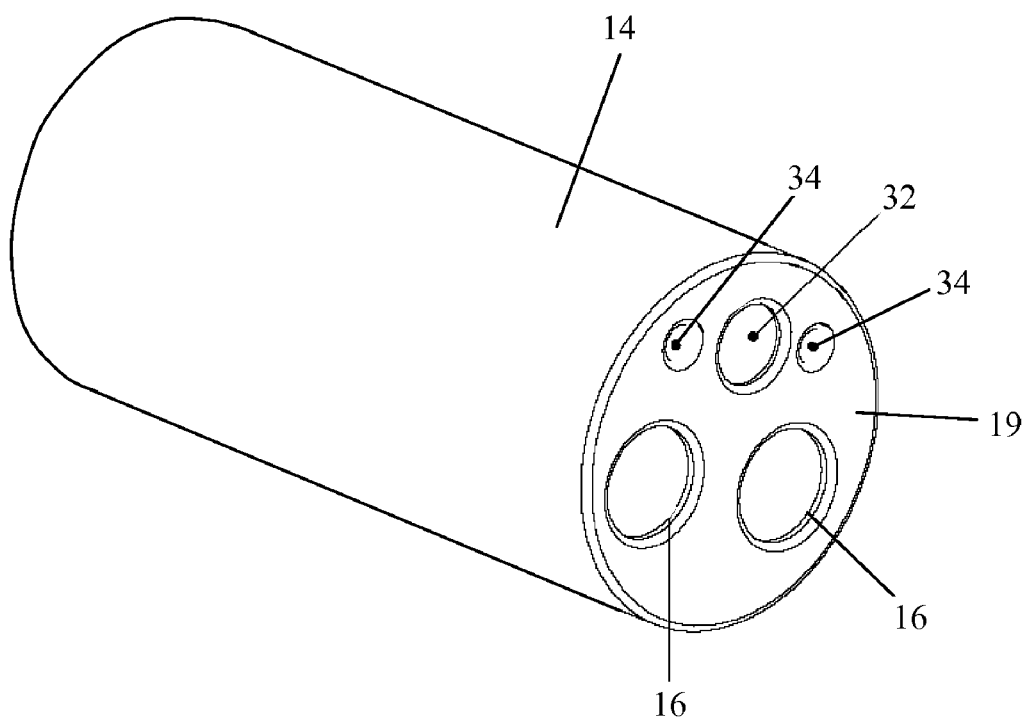
FIG. 2 shows a perspective view of the distal end of an insertion tube of the endoscope of FIG. 1.

As shown in FIG. 2, the insertion tube 14 of the endoscope 10 has two longitudinal channels 16. In general, however, the insertion tube 14 may have any number of longitudinal channels. Each longitudinal channel 16 allows an instrument to reach the body cavity to perform any desired procedures such as to take samples of suspicious tissues or to perform other surgical procedures such as polypectomy. The instruments may be, for example, a retractable needle for drug injection, hydraulically actuated scissors, clamps, grasping tools, electrocoagulation systems, ultrasound transducers, electrical sensors, heating elements, laser mechanisms and other ablation means. In some embodiments, one of the channels can be used to supply a washing liquid such as water for washing. Another or the same channel may be used to supply a gas, such as $CO_2$ or air into the organ. The channels 16 may also be used to extract liquids or inject liquids, such as a drug in a liquid carrier, into the body.

The insertion tube 14 preferably is steerable or has a steerable distal end region 18 as shown in FIG. 1. The length of the distal end region 18 may be any suitable fraction of the length of the insertion tube 14, such as one half, one third, one fourth, one sixth, one tenth, or one twentieth. The insertion tube 14 may have control cables (not shown) for the manipulation of the insertion tube 14. Preferably, the control cables are symmetrically positioned within the insertion tube 14 and extend along the length of the insertion tube 14. The control cables may be anchored at or near the distal end 19 of the insertion tube 14. Each of the control cables may be a Bowden cable, which includes a wire contained in a flexible overlying hollow tube. The wires of the Bowden cables are attached to controls 20 in the handle 22 (FIG. 1). Using the controls 20, the wires can be pulled to bend the distal end region 18 of the insertion tube 14 in a given direction.

As shown in FIG. 1, the endoscope 10 may also include a control handle 22 connected to the proximal end 24 of the insertion tube 14. Preferably, the control handle 22 has one or more ports and/or valves (not shown) for controlling access to the channels 16 of the insertion tube 14. The ports and/or valves can be air or water valves, suction valves, instrumentation ports, and suction/instrumentation ports. As shown in FIG. 1, the control handle 22 may additionally include buttons 26 for taking pictures with an imaging device on the insertion tube 14.

The proximal end 28 of the control handle 22 may include an accessory outlet 30 (FIG. 1) that provides fluid communication between the air, water and suction channels and the pumps and related accessories. The same outlet 30 or a different outlet can be used for electrical lines to light and imaging components at the distal end of the endoscope 10.

As shown in FIG. 2, the endoscope 10 also includes an imaging device 32 and light sources 34, both of which are disposed at the distal end 19 of the insertion tube 14. The imaging device 32 may include, for example, a lens, single chip sensor, multiple chip sensor or fiber optic implemented devices. The imaging device 32, in electrical communication with a processor and/or monitor, may provide still images or recorded or live video images. The light sources 34 may be light emitting diodes (LEDs) or fiber optical delivery of light from an external light source. The light sources 34 preferably are equidistant from the imaging device 32 to provide even illumination. The intensity of each light source 34 can be adjusted to achieve optimum imaging. The circuits for the imaging device 32 and light sources 34 may be incorporated into a printed circuit board (PCB).

Figure 3A:
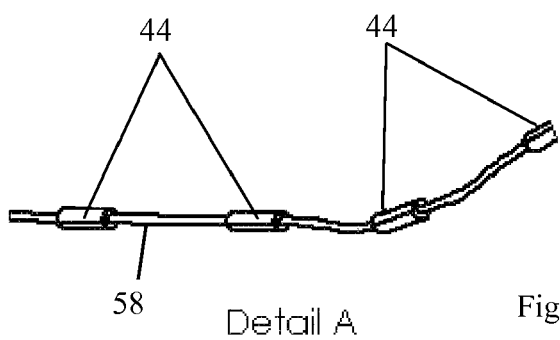
FIG. 3A shows a detailed perspective view of a segment of the vibratory device shown in FIG. 3.
Figure 3:
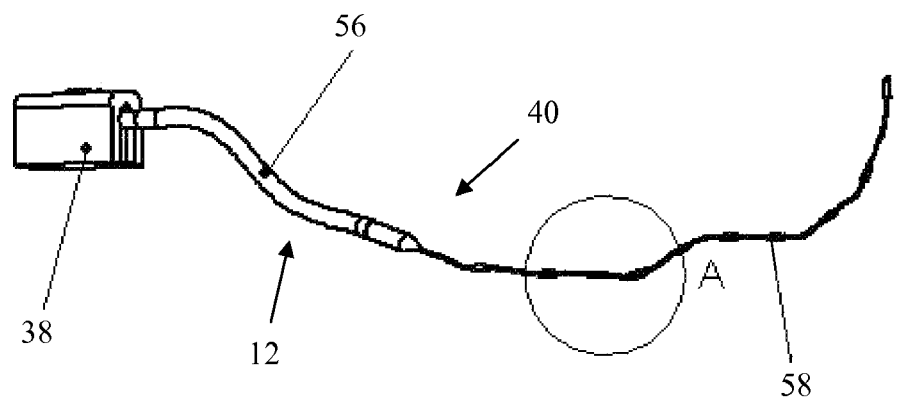
FIG. 3 shows a perspective view of a vibratory device of the endoscope shown in FIG. 1.

FIGS. 3 and 3A illustrate the vibratory device 12 of the endoscope 10. The vibratory device 12 includes a motor assembly 38 and a torque transmission cable 40. The motor assembly 38 includes a motor housing 42 and a motor (not shown) disposed in the motor housing 42. The transmission cable 40 includes off-balance masses 44 and may be rotated by the motor of the motor assembly 38 so that the off-balance masses 44 impart vibrations to the transmission cable 40.

Figure 4:
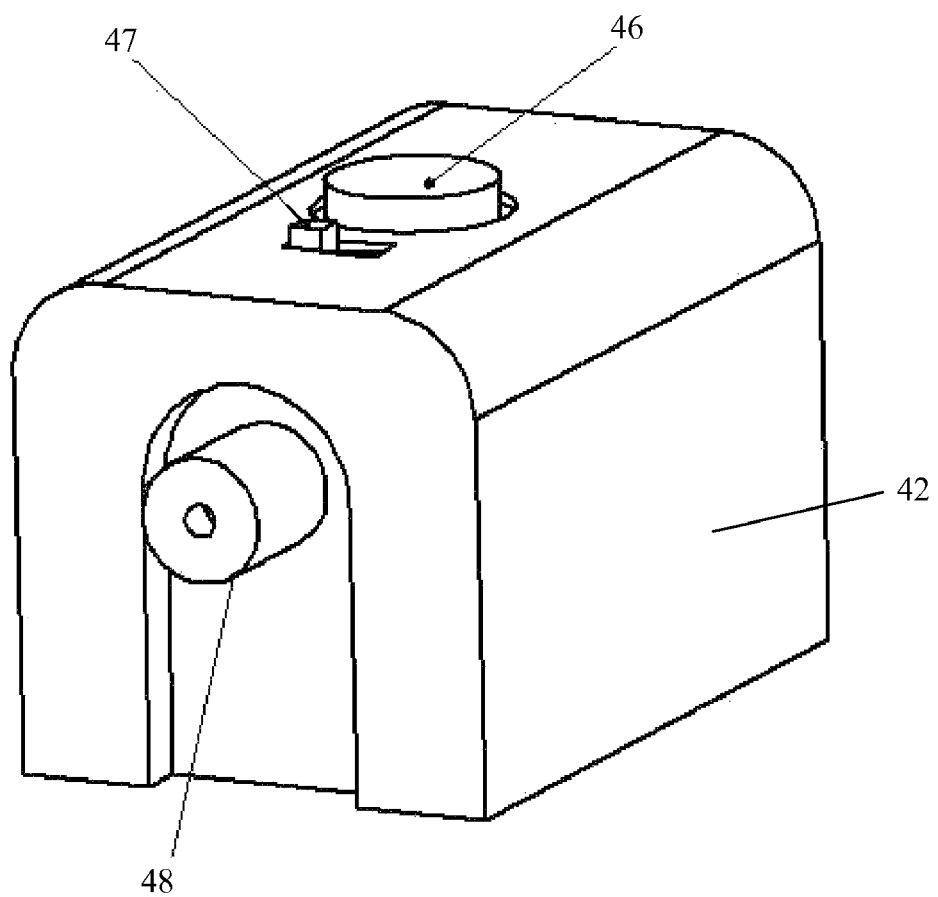
FIG. 4 shows a perspective view of the motor assembly of the vibratory device shown in FIG. 3.

FIG. 4 provides a more detailed view of the motor assembly 38. The motor assembly 38 may includes a power switch 46 and a speed adjustor 47. The power switch 46 is used to turn on or turn off the motor assembly 38, and the speed adjustor 47 is used to control the speed of the motor. The motor may be a direct current (DC) motor. The direct current supplied to the motor may be converted from an alternating current (AC), and the motor assembly 38 may include an inverter (not shown) for this purpose. The inverter may be placed inside the motor housing 42 or incorporated into the power plug (not shown) of the motor assembly 38. In addition, the motor assembly 38 may include a variable transformer, which can be adjusted by the speed adjustor 47 to vary the voltage to the motor in order to control motor speed. In addition to or as an alternative to AC power, one or more batteries may be used to supply DC power to the motor. In some embodiments, the motor may be integrated into the handle 22 of the endoscope 10. All electrical components of the motor assembly 38 may be disposed in the motor housing 42.

Figure 5:
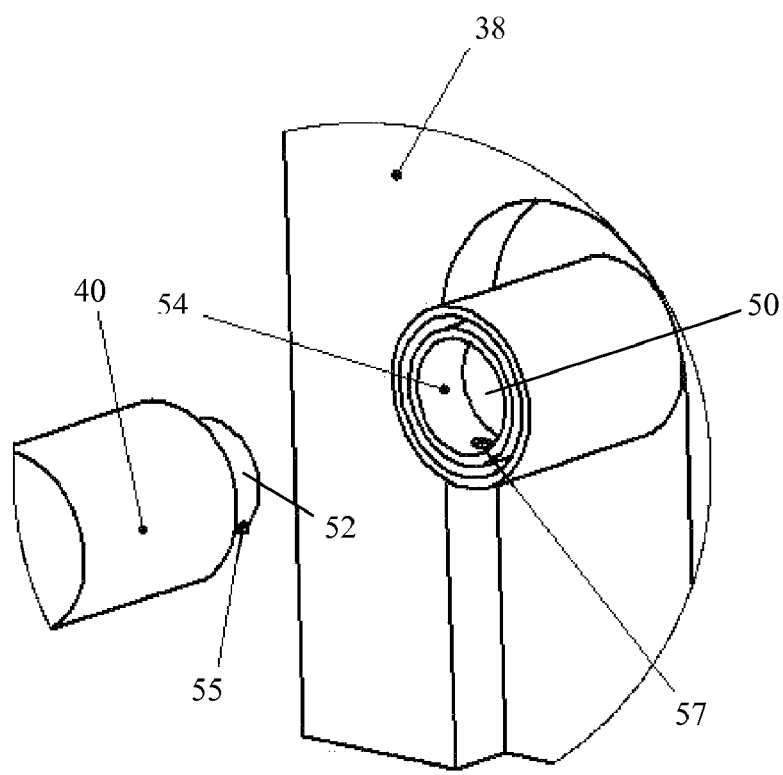
FIG. 5 shows an interface between the motor shaft and the transmission cable of the vibratory device shown in FIG. 3.

FIG. 5 illustrates how in the illustrated embodiment the shaft 50 of the motor is connected to the proximate end 52 of the transmission cable 40. In general, however, the motor shaft 50 may be connected to the proximate end 52 of the transmission cable 40 in any suitable manner. In FIG. 5, the vibratory device 14 includes a sleeve-shaped interface 54 that connects the motor shaft 50 to the proximate end 52 of the transmission cable 40. The proximate end 52 of the transmission cable 40 and the motor shaft 50 preferably extend into the interface 54 from different ends of the interface 54. The transmission cable 40 and the motor shaft 50 may be connected to the interface 54 via an engagement mechanism such as detent springs, mechanical keying features or threaded fasteners. In the illustrated embodiment, each of the transmission cable 40 and the motor shaft 50 includes one or more spring loaded ball-nose plungers 55 that mate with complementary notches 57 on the interior surface of the interface 54. In some alternative embodiments, the sleeve-shaped interface 54 may be an integral part of the motor shaft 50, and the proximate end 52 of the transmission cable 40 may engage the interface 54 as described above. Or the sleeve-shaped interface 54 may be an integral part of the proximate end 55 of the transmission cable 40, and the motor shaft 50 may engage the interface 54 as described above. The above-described connection between the motor shaft 50 and the proximate end 52 of the transmission cable 40 allows for the transmission of torque between the motor shaft 50 and the transmission cable 40, while also allowing for a quick attachment or detachment between the motor shaft 50 and the transmission cable 40.

As illustrated in FIG. 3, the transmission cable 40 may include a first section 56 and a second section 58. The first section 56 may be an interconnecting section, and the second section 58 may be a distal section. Preferably, the second section 58 is designed to extend through a longitudinal channel 16 of the insertion tube 14, and the off-balance masses 44 are placed in the second section 58. The second section 58 preferably is as flexible as the insertion tube 14. The first section 56 allows the placement of the motor assembly 38 away from the insertion tube 14.

Figure 6:
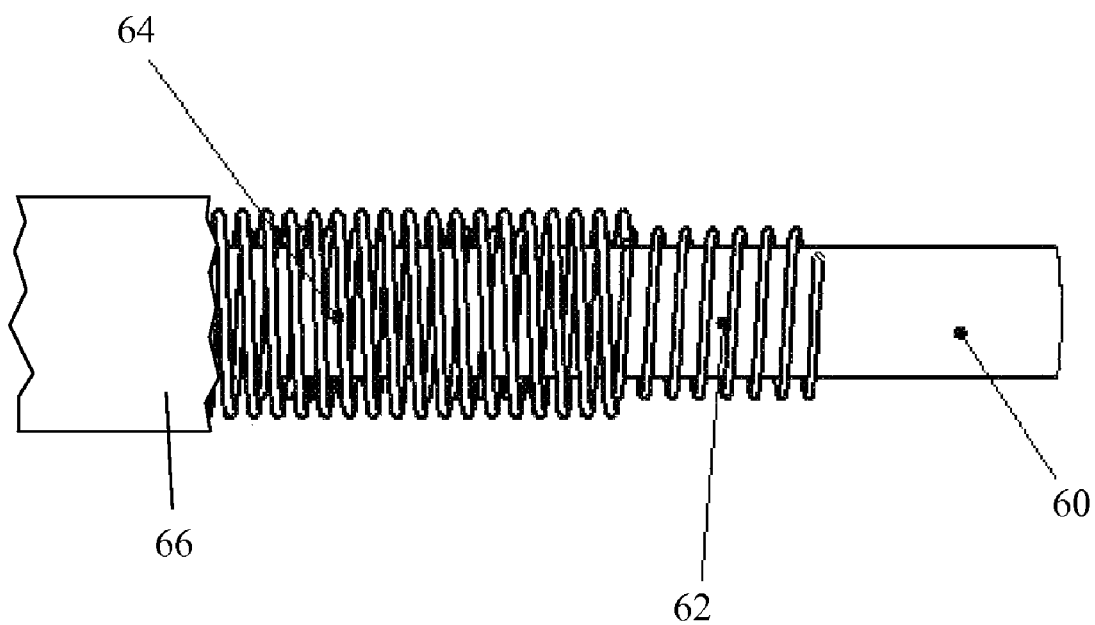
FIG. 6 shows a cut away view of the transmission cable of the vibratory device shown in FIG. 3.

In the illustrated embodiment, as shown in FIG. 6, the first section 56 of the transmission cable 40 has a core 60, two layers 62, 64 of metal wires that surround the core 60, and a flexible tube 66 that surrounds the core 60 and layers 62, 64 to protect them. In the preferred embodiment, the first section 56 includes engagement interfaces on both ends. On one end, the first section 56 preferably includes the proximate end 52 of the transmission cable 40 that is rotationally engaged with the motor shaft 48 (FIG. 5). On the other end, the first section 56 includes an interface that can be suitably connected to the second section 58. For example, this interface of the first section 56 may include notches that engage spring loaded ball-nose plungers on the second section 58, just like how the proximate end 50 of the transmission cable 40 is connected to the motor shaft 48.

The second section 58 of the transmission cable 40 may be similar to the first section 56 and may include a core 60, two layers 62, 64 of metal wires that surround the core 60, and a flexible tube 66 that surrounds the core 60 and layers 62, 64. The second section 58 may have a smaller diameter than the first section 56. In some embodiments, as shown in FIG. 3A, the off-balance masses 44 are not covered by the flexible tube 66. In some other embodiments, the off-balance masses 44 are covered by the flexible tube 66, and the vibration caused by the rotating off-balance masses 44 is transmitted to the flexible tube 66 and, when the second section 58 is inserted into the insertion tube 14, from the flexible tube 66 to the insertion tube 14.

Figure 7:
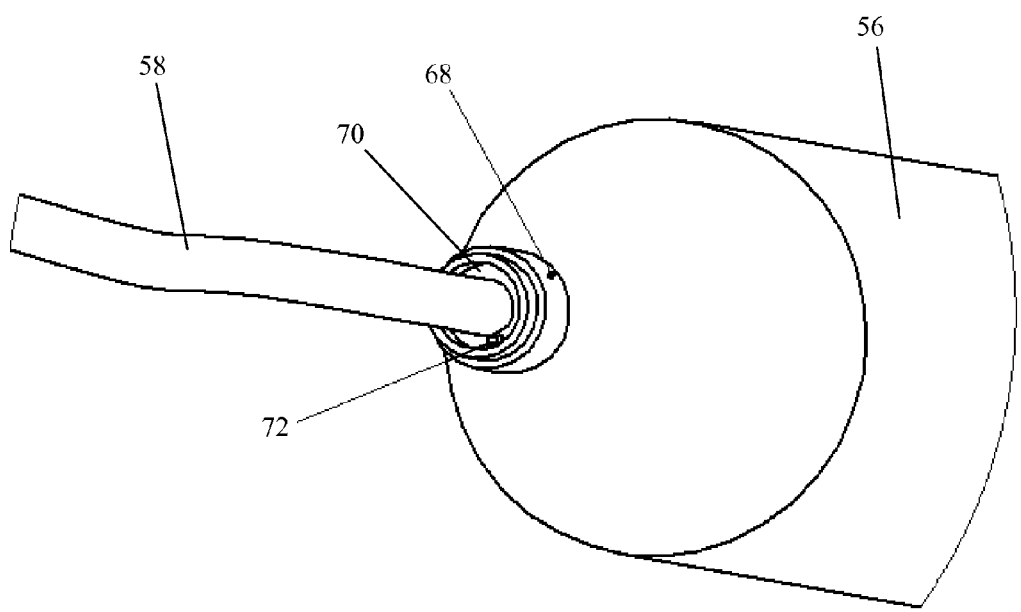
FIG. 7 shows a perspective view of a connector and a safety switch at the interface between the first and second sections of the transmission cable.
Figure 8:
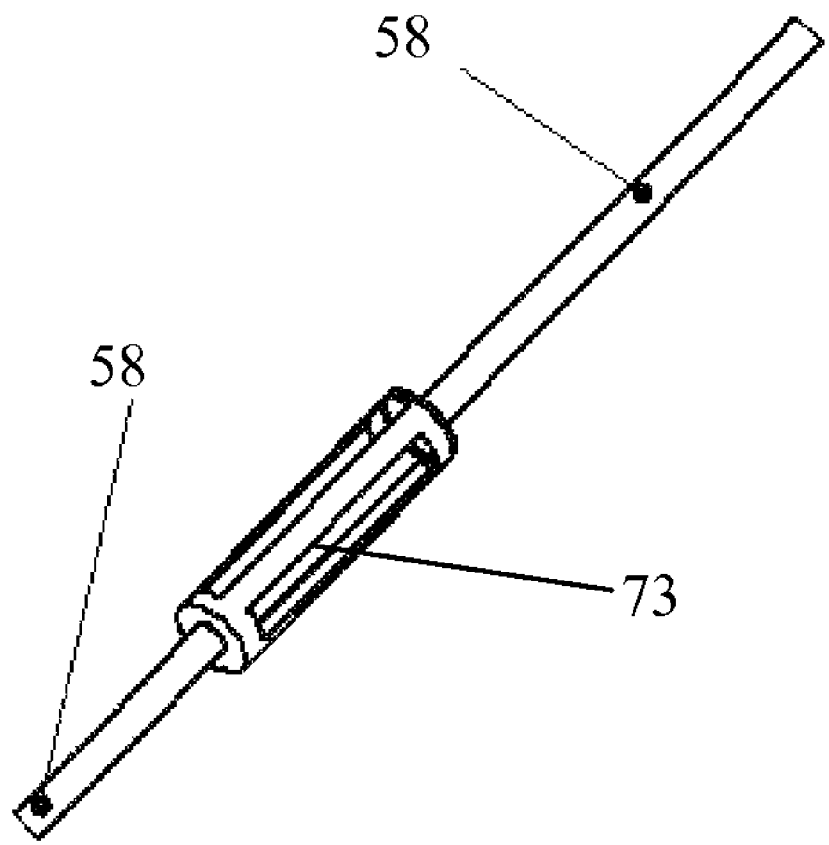
FIG. 8 shows a perspective view of a cage used in the vibratory device shown in FIG. 3.

As shown in FIG. 7, the second section 58 may also include a connector 68 at its proximal interface with the first section 56. The connector 68, preferably made of a flexible material such as rubber, may have a generally cylindrical configuration with a circular groove 70 at its end. When the second section 58 is fully and securely inserted into the longitudinal channel 16 of the insertion tube 14, the groove 70 preferably receives, and is secured to, the tubular end of the insertion tube's longitudinal channel 16. This ensures that the transmission cable 40 moves together with the insertion tube 14, as the physician advances the endoscope 10 through the body cavity.

The second section 58 may further include a safety switch 72 as illustrated in FIG. 7. Preferably, the safe switch 72 is placed at the bottom of the circular groove 70 of the connector 68. When the second section 58 is fully and securely inserted into the insertion tube's longitudinal channel 16, the tubular end of the longitudinal channel 16 preferably reaches the bottom of the circular groove 70 to contact the safety switch 72 to activate it. The motor cannot operate without the activation of this switch 72, preventing the use of the vibratory device 12 outside the insertion tube 14. Electrical wires may extend through the transmission cable 40 to connect the safety switch 72 to the motor for transmitting a signal from the switch 72 to the motor.

The second section 58 may additionally include a removable flexible sheath (not shown). The sheath may be removed when the second section 58 is to be inserted into the insertion tube 14. The sheath protects the components of the second section 58, such as the off-balance masses 44, when the vibratory device 12 is not in operation. Additionally, the transmission cable 40 including the off-balance masses 44 may be coated with a polymer that prevents wear to the inner surface of the longitudinal channel 16 of the insertion tube 14.

Figure 12:
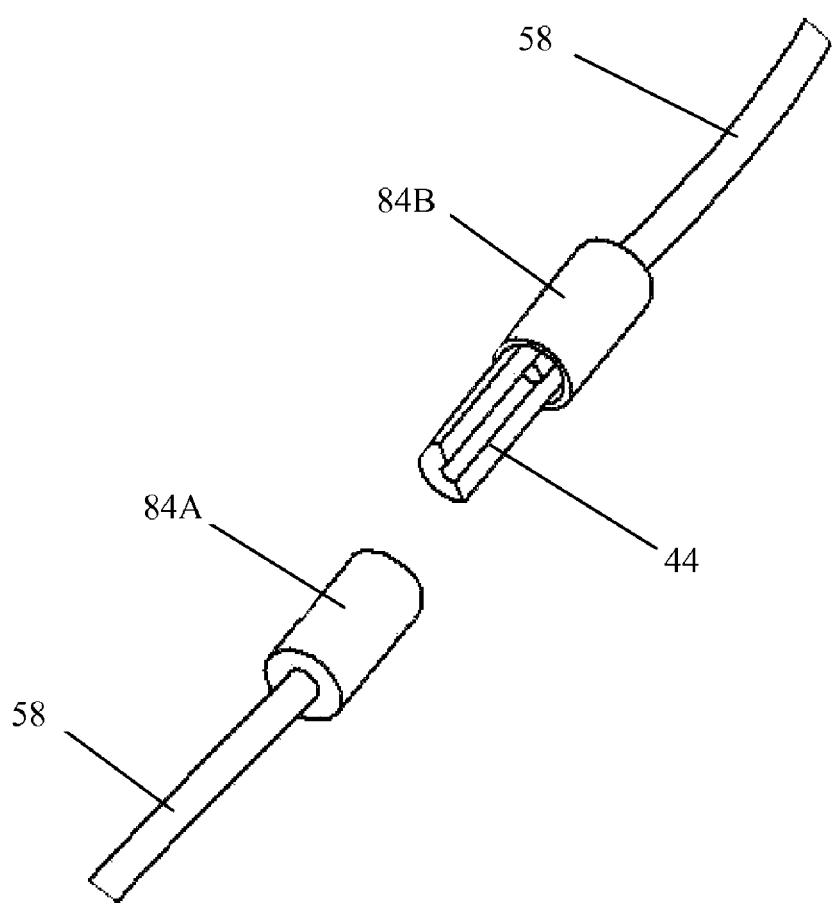
FIGS. 12 and 13 show different perspective views of a further alternate embodiment of the off-balance mass.

In another embodiment, the torque transmission cable 40 provides a fluid conduit that can be used to suck fluid from the body cavity or supply fluid to the body cavity during a procedure. This fluid conduit may be provided in any suitable manner. For example, the transmission cable 40 may retain the two layers 62, 64 of coiled metal wires, but the solid core 60 may be removed to provide the transmission cable 40 with a hollow central lumen. The final mass on the transmission cable 40 may include a hole in order to allow suction through the hole and into the lumen of the transmission cable 40. Additionally, the insertion tube' channel 16, in which the transmission cable 40 is inserted, may still be used to suck fluid from the body cavity or supply fluid to the body cavity. To that end, the transmission cable 40 may include one or more metal cages 73 that, as illustrated in FIG. 12, allow air or fluid to pass through them and at same time can transmit torque. One of the metal cages 73 may be situated proximally in the endoscope 10 such that the suction port on the endoscope's handle 22 can be employed to perform the necessary operation even with the transmission cable 40 in the channel 16. The connector 68 at the proximal end of the second section 58 may serve as a seal over the opening of the channel 16 in order to allow suction.

In some embodiments, the vibratory device 12 may be integrated into the endoscope 10. This may be accomplished, for example, by integrating or disposing the transmission cable 40 in a dedicated channel of the endoscope 10. The power switch, speed adjustor, and/or the motor of the vibratory device 12 may be placed on the handle 22 of the endoscope 10.

The off-balance masses 44 may be arranged and mounted in the second section 58 of the transmission cable 40 in any suitable manner. For example, the off-balance masses 44 may be arranged at a set interval or at variable intervals in the second section 58. The spacing of the off-balance masses 44 may affect the oscillatory pattern of the transmission cable 40. Masses that are spaced too closely or too far may not generate vibrations of sufficient magnitude to affect looping. The angle of orientation from one set of masses to the next will determine the shape of the vibration along the transmission cable 40. The off-balance masses 44 may have the same weight or different weights and/or the same offset or different offsets between the off-balance masses' centers of mass and their axes of rotation. In many cases, an off-balance mass's axis of rotation is the same or substantially the same as the longitudinal axis of the transmission cable 40.

Figure 9:
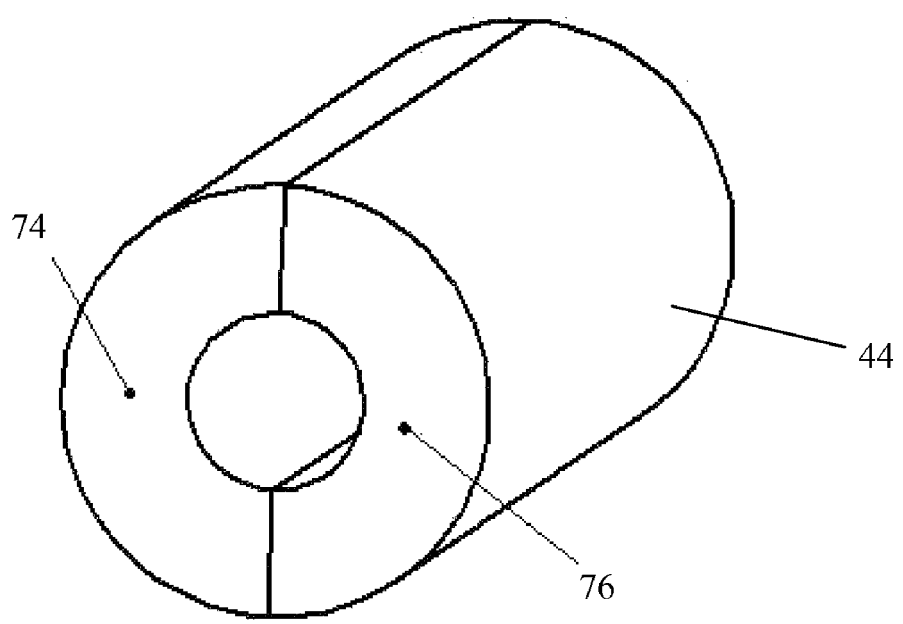
FIG. 9 shows a perspective view of an off-balance mass of the vibratory device shown in FIG. 3.

The offset between each off-balance mass's center of mass and its axis of rotation may be created in any suitable manner. In the illustrated embodiment, for example, an off-balance mass 44 may be constructed from at least two different materials as shown in FIG. 9. One part 74 (such as one half) of the off-balance mass 44 may be made from a heavier material (i.e., a material with a higher density) such as a metallic material (for example, iron or copper), while the other part 76 (such as the other half) may be made from a lighter material (i.e., a material with a lower density) such as a plastic material (for example, polyurethane). Additionally, the two parts of the off-balance mass may have different volumes with one of the parts being larger than the other part.

Figure 10:
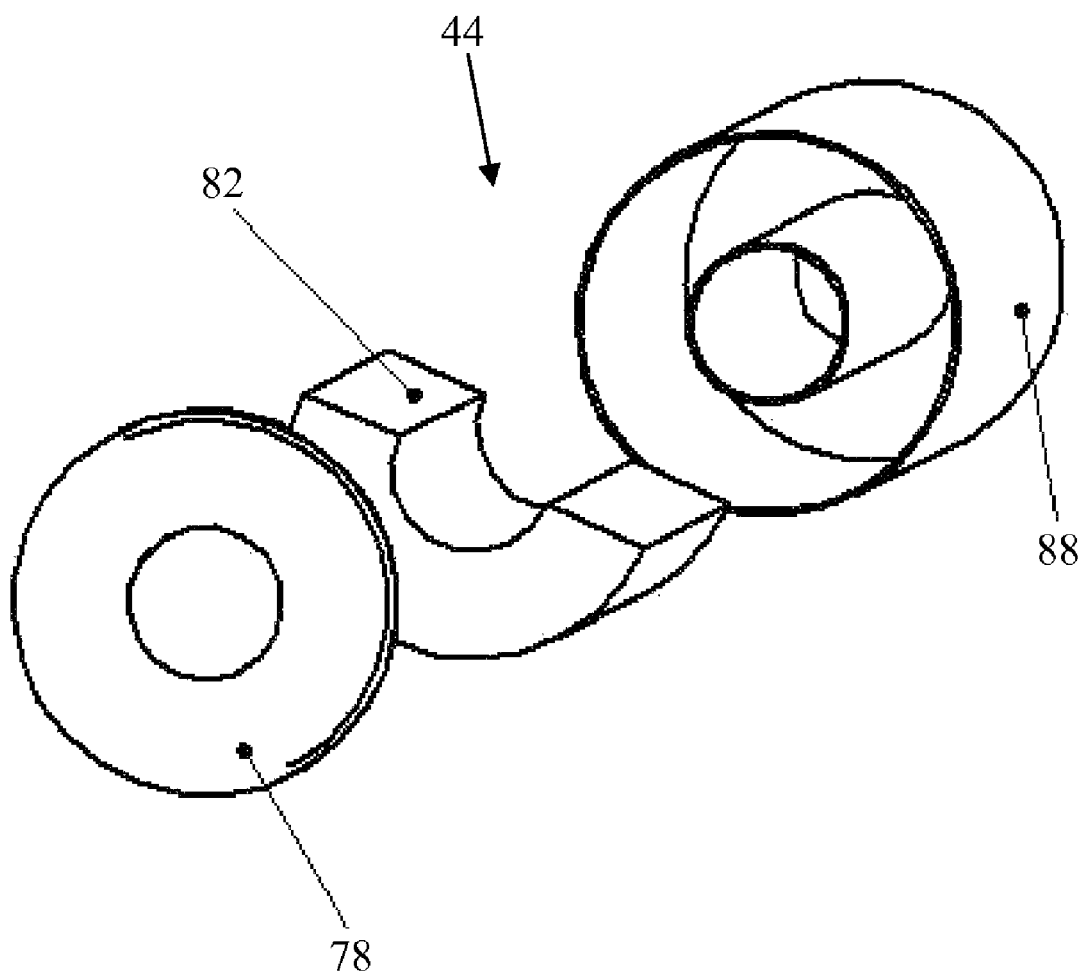
FIG. 10 shows an exploded view of an alternate embodiment of the off-balance mass.

Alternatively, an off-center mass 44 may be constructed from at least a cap 78, a housing 80, and a mass 82, as shown in FIG. 10. The cap 78 and housing 80 may be made from a light metal such as aluminum, while the mass 82 may be made from a heavier metal such as iron. As shown in FIG. 10, the mass 82 occupies about one half of the housing 80, although the mass may occupies any portion (but not all) of the housing 80. The cap 78 is used to secure the mass 82 in the housing 80.

Figure 11:
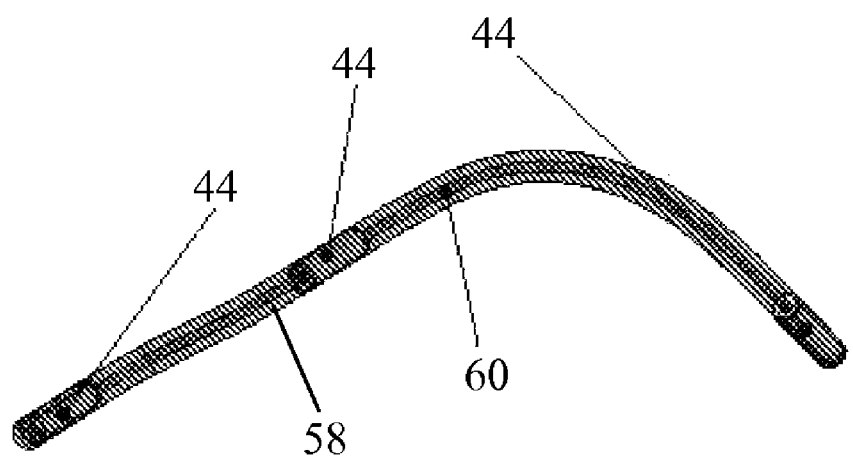
FIG. 11 shows a perspective view of another alternate embodiment of the off-balance mass.

In another embodiment, as shown in FIG. 11, the off-balance masses 44 may be integrated inside the transmission cable 40. As the transmission cable 40 is constructed, the off-balance masses 44 preferably are simultaneously integrated. The off-balance masses 44 may be disposed between the core 60 and the layers 62, 64 of metal wires and may be secured there by means of, for example, overmolding, extruding, and using an adhesive.

Figure 13:
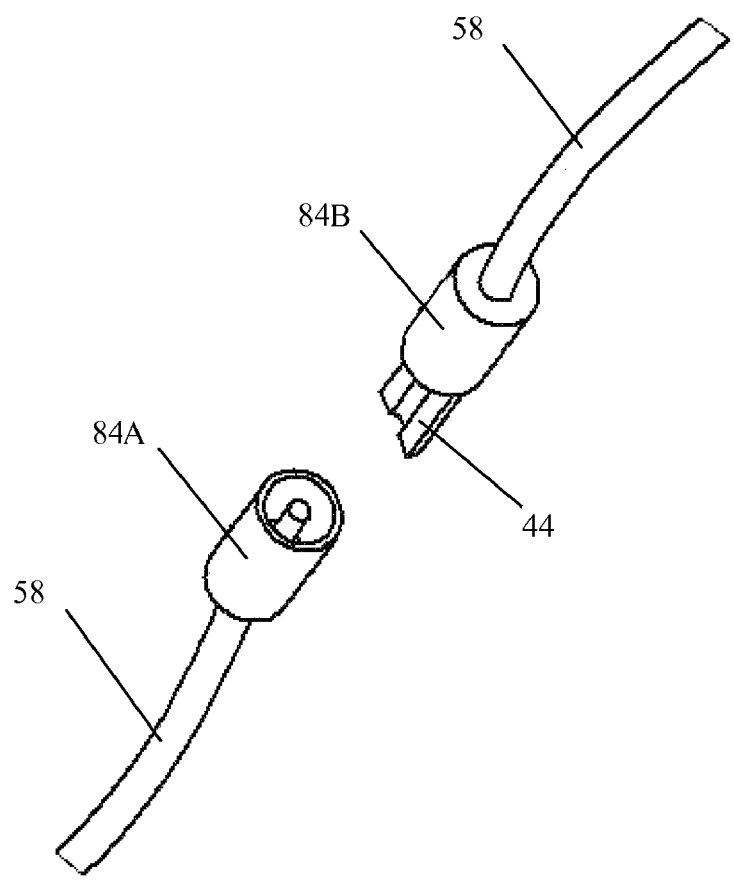

In a further embodiment, as shown in FIGS. 12 and 13, an off-balance mass 44 is part of a connector 84A, 84B that joins two segments of the transmission cable 40. This allows the customization of the length of the transmission cable 40. In this embodiment, the connector 84A, 84B includes two housing segments 84A, 84B and an off-balance mass 44 disposed in the housing 84A, 84B. The two housing segments 84A, 84B are joined to each other to form the housing 84A, 84B.

In a still further embodiment, the final off-balance mass 44 on the distal end of the transmission cable 40 may be tapered. This feature facilitates entry of the vibratory device 12 into a channel 16 of the insertion tube 14. Preferably, the final off-balance mass 44 has the previously-described cylindrical mass assembly and a conical section attached to the cylindrical mass assembly by any suitable means such as welding, overmolding, and using an adhesive.

The off-balance masses 44 may be mounted to the transmission cable 40 in any suitable manner. In the illustrated embodiment, for example, the off-balance masses 44 may be mounted to the transmission cable 40 by ultrasonic welding, overmolding, and using an adhesive.

In operation, the motor of the vibratory device 12 rotates the transmission cable 40 and the off-balance masses 44 in the transmission cable 40. Each rotating off-balance mass 44 generates a centrifugal force that is equal to $F = M \cdot R \cdot \omega^2$, where F is the centrifugal force, M is the mass, $\omega$ is the angular velocity, and R is the distance between the off-balance mass's center of mass and its axis of rotation. The centrifugal force in any particular radial direction (i.e., any direction that is perpendicular to the longitudinal direction of the transmission cable 40) oscillates in a sinusoidal pattern. This oscillatory centrifugal force imparts vibration to the transmission cable 40. This principle of rotating an off-balance mass to induce vibration is the basis for vibratory devices such as electric toothbrushes and is well documented and understood in the consumer electronics art. The oscillations create the vibrations necessary to prevent the buildup of looping-causing frictional forces when an endoscope 10 is advanced through the body cavity.

During a procedure, after connecting the torque transmission cable 40 to the motor assembly 38 to assemble the vibratory device 12, a physician can insert the vibratory device 12 into a channel 16 of the endoscope's insertion tube 14. In some cases, the vibratory device 12 is not advanced to the steerable end region 18 of the insertion tube 14 to maintain the steerability of the end region 18. The endoscope 10 is then advanced through the patient's body cavity. If looping begins to occur, the physician turns on the motor to vibrate the insertion tube 14. The vibrations mitigate looping effects by reducing the buildup of frictional forces between the body cavity and the insertion tube 14. Since the insertion tube 14 is vibrating, any given segment of the insertion tube 14 is only in contact with the body cavity for a brief moment of time. This prevents frictional forces from causing looping. The physician may vary, as needed, the characteristics (such as the intensity) of the oscillations by adjusting the speed adjustor 47. Once the endoscope 10 is placed in the body cavity, the physician may turn off the motor and remove the vibratory device 14 from the channel 16 of the endoscope's insertion tube 14. The physician is then free to use the longitudinal channel 16 for other purposes as she performs the regular procedure. After the medical procedure is complete, the transmission cable 40 (or the second section 58 thereof) may be disconnected and, in some cases, disposed of.

The aforementioned order of events is only one of many possibilities. For example, the vibratory device 14 may also be inserted into the insertion tube 14 after looping has occurred. The vibratory device 14 may even be removed and inserted as needed in order to accommodate other uses of the longitudinal channel 16.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

The invention claimed is:

1. An endoscope assembly, comprising:
   an insertion tube including a channel, a light source, and an imaging device; and
   a mechanical vibratory device disposed within the channel of the insertion tube, the vibratory device including:
      a flexible transmission cable having a longitudinal axis and being configured to rotate with respect to the insertion tube; and
   a plurality of masses coupled to the flexible transmission cable, each mass having a non-uniform weight distribution about the longitudinal axis of the flexible transmission cable such that each mass has a center of mass that is offset from the longitudinal axis, and wherein the vibratory device being configured to vibrate the insertion tube within a body cavity to limit frictional forces between the insertion tube and the body cavity and inhibit looping of the insertion tube within the body cavity.

2. The endoscope assembly of claim 1, wherein the insertion tube and the vibratory device are integrally formed.

3. The endoscope assembly of claim 1, wherein the vibratory device includes a motor configured to rotate the flexible transmission cable.

4. The endoscope assembly of claim 3, wherein the flexible transmission cable includes a first section connected to the motor and a second section connected to the first section, and wherein the first section has a larger cross-section than the second section.

5. The endoscope assembly of claim 3, wherein the flexible transmission cable includes a first section connected to the motor and a second section connected to the first section, and wherein the masses are coupled to the second section of the flexible transmission cable.

6. The endoscope assembly of claim 1, wherein the vibratory device includes a sheath that encloses at least a portion of the flexible transmission cable.

7. The endoscope assembly of claim 1, wherein each mass includes two portions, a first portion having a greater density than a second portion.

8. The endoscope assembly of claim 1, wherein each mass includes two portions, a first portion having a greater weight than a second portion.

9. The endoscope assembly of claim 1, wherein each mass assembly includes a housing and a mass disposed in the housing.

10. The endoscope assembly of claim 1, wherein
    the flexible transmission cable includes a first section and a second section connected to the first section; and
    a power switch positioned between the first and second sections.

11. The endoscope assembly of claim 1, wherein
    the flexible transmission cable includes a first section and a second section connected to the first section; and
    a seal positioned between the first and second sections.

* * * * *